United States Patent
Schor

(10) Patent No.: US 10,495,711 B2
(45) Date of Patent: Dec. 3, 2019

(54) SYSTEM AND METHOD FOR COMPARING SYSTEM CONFIGURATIONS FOR MAGNETIC RESONANCE TOMOGRAPHY UNITS

(71) Applicant: Stefan Schor, Erlangen (DE)

(72) Inventor: Stefan Schor, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 110 days.

(21) Appl. No.: 15/673,652

(22) Filed: Aug. 10, 2017

(65) Prior Publication Data

US 2018/0128890 A1 May 10, 2018

(30) Foreign Application Priority Data

Aug. 11, 2016 (EP) .................................. 16183821

(51) Int. Cl.
- G01V 3/00 (2006.01)
- G01R 33/54 (2006.01)
- G16H 40/63 (2018.01)

(52) U.S. Cl.
CPC .......... G01R 33/543 (2013.01); G16H 40/63 (2018.01)

(58) Field of Classification Search
CPC ............. G01R 33/543; G01R 33/5659; G01R 33/3415; G01R 33/36; A61B 5/055
USPC ......................................................... 324/309
See application file for complete search history.

(56) References Cited

U.S. PATENT DOCUMENTS

| 8,856,292 B2 | 10/2014 | Srinivasan | |
| 8,856,293 B1 * | 10/2014 | Sadry | G06F 3/067 709/211 |
| 2008/0072151 A1 * | 3/2008 | Song | G06F 3/0481 715/708 |
| 2008/0108891 A1 | 5/2008 | Campagna | |

(Continued)

FOREIGN PATENT DOCUMENTS

| CN | 105247382 A | 1/2016 |
| DE | 102012215110 A1 | 3/2014 |

OTHER PUBLICATIONS

European Search Report for related European Application No. 16183821.4 dated Nov. 30, 2016.

(Continued)

*Primary Examiner* — Clayton E. LaBalle
*Assistant Examiner* — Frederick Wenderoth
(74) *Attorney, Agent, or Firm* — Lempia Summerfield Katz LLC

(57) ABSTRACT

Systems and methods are provided for comparing a system configuration of a magnetic resonance tomography unit. The magnetic resonance tomography unit includes a controller and an output unit. The configuration device includes a controller and an input unit. A data storage device includes a data connection with the magnetic resonance tomography unit via a first data link and with the configuration device via a second data link. A first system configuration of the magnetic resonance tomography unit is stored on the data storage device. The magnetic resonance tomography unit generates an identification for the first system configuration and outputs the identification. The configuration device detects the identification with the input unit and accesses the first system configuration in the data storage device using the identification.

14 Claims, 2 Drawing Sheets

(56) References Cited

U.S. PATENT DOCUMENTS

| | | | |
|---|---|---|---|
| 2011/0129056 A1* | 6/2011 | Allmendinger | A61B 5/02405 378/4 |
| 2014/0059259 A1* | 2/2014 | Kalnischkies | G06F 15/177 710/104 |
| 2015/0200996 A1* | 7/2015 | Ziarati | H04L 67/02 709/201 |
| 2015/0230760 A1* | 8/2015 | Schneider | A61B 90/96 600/300 |

OTHER PUBLICATIONS

Chinese Office Action for related Chinese Patent Application No. 201710674744.5, dated Jun. 27, 2019, with English translation.

\* cited by examiner

1 - Magnetic resonance tomography unit
2 - Longitudinal direction
10 - Magnetic unit
11 - Field magnet
12 - Gradient coils
14 - Body coil
16 - Patient tunnel 20 - Control unit
21 - Gradient controller
22 - High-frequency unit
23 - Controller
25 - Signal bus
26 - Output unit
27 - First data link 30 - Examination table
31 - Signal link
40 - Patient
50 - Local coil
60 - Data storage device
70 - Configuration device
71 - Input unit
72 - Second data link

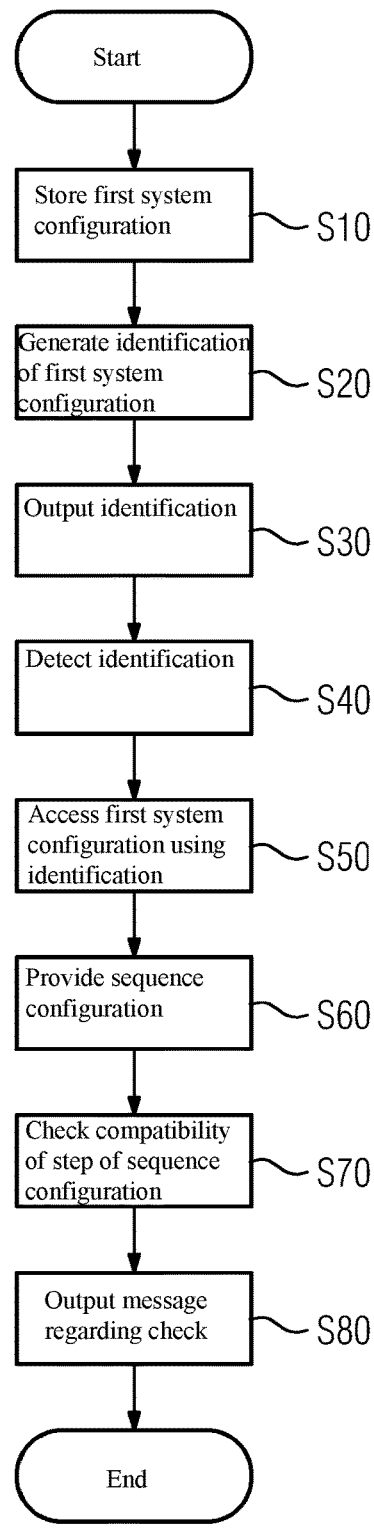

SYSTEM AND METHOD FOR COMPARING SYSTEM CONFIGURATIONS FOR MAGNETIC RESONANCE TOMOGRAPHY UNITS

CROSS REFERENCE TO RELATED APPLICATIONS

This application claims the benefit of EP16183821, filed on Aug. 11, 2016, which is hereby incorporated by reference in its entirety.

FIELD

Embodiments relate to comparing system configurations for a magnetic resonance tomography unit.

BACKGROUND

Magnetic resonance tomography units are imaging devices that for mapping an examination object, orient nuclear spins of the examination object using a strong external magnetic field and excite the nuclear spins to precession around the orientation by way of a magnetic alternating field. The precession or return of the spins from the excited state into a state with lower energy generates a magnetic alternating field, also called a magnetic resonance signal, as a response, that is received by antennae.

With the aid of magnetic gradient fields, a spatial encoding is impressed on the signals, that subsequently provides allocation of the received signal to a volume element. The received signal is evaluated and a three-dimensional imaging representation of the examination object supplied.

The presentation that is generated gives a spatial density distribution of the spins.

Examinations using magnetic resonance tomography units may be automated by configuration files that describe and control the sequences of the individual components of the magnetic resonance tomography unit during the examination. There are different options variants of the hardware (e.g., different number of receiving and transmitting channels or different local coils) and different software modules even in identical magnetic resonance tomography units from the same manufacturer.

For reasons of cost efficiency, magnetic resonance tomography units may be optimally used to capacity by examinations and not by the preparation and inputting of configurations and examination procedures. The configuration files are therefore compiled on configuration devices (e.g., computers or workstations) using specific software. Due to the different hardware and software options, the situation repeatedly occurs where a configuration file then cannot be executed when played in a magnetic resonance tomography unit owing to the different options variants, and requires expensive system time for adjustment or conversion.

SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide for making the configuration of a magnetic resonance tomography unit faster, safer and less expensive.

In an embodiment, a method is provided for comparing a first system configuration of a magnetic resonance tomography unit with a configuration device with the aid of a data storage device. A system configuration refers to an accumulation of information that summarizes or describes all parameters of the magnetic resonance tomography unit that influence the execution of configuration files. The parameters may be, for example, software version, software modules, hardware options or also auxiliary equipment. The data storage device is configured to store a plurality of system configurations from a plurality of magnetic resonance tomography units.

The magnetic resonance tomography unit includes a controller and an output unit. The configuration device includes a controller and an input unit. The output unit and the input unit are compatible with each other to the extent that information output by the output unit of the magnetic resonance tomography unit may be detected by the input unit configuration device.

There is a first data link between magnetic resonance tomography unit and data storage device and there is a second data link between configuration device and data storage device. The configuration device and the magnetic resonance tomography unit have access to the data storage device. The first or second data links may be, for example, a local network or the Internet, or also point-to-point data links.

In an embodiment, the controller of the magnetic resonance tomography unit stores a first system configuration of the magnetic resonance tomography unit on the data storage device.

The controller generates an identification of the first system configuration. An identification refers to a unique allocation of the first system configuration to the magnetic resonance tomography unit. Furthermore, the identification may also provide access to the first system configuration on the data storage device. The identification may also have, for example, a path or link.

The magnetic resonance tomography unit outputs the identification via the output unit. Different options of outputting may be used.

The input unit of the configuration device detects the identification.

The configuration device accesses the first system configuration in the data storage device via the data link with the aid of the identification. For example, the configuration unit loads the first system configuration or parts thereof into an internal storage device in order to use information from the first system configuration for the creation of a sequence configuration.

Embodiments provide that the correct system configuration is taken as a basis when creating a sequence configuration for a magnetic resonance tomography unit, and unnecessary rectification is therefore avoided. Double data storage is avoided and unauthorized access to the systems is difficult.

The magnetic resonance tomography unit includes a controller and an output unit. The controller of the magnetic resonance tomography unit is configured to store a first system configuration in a data storage device for a plurality of system configurations via a data link. Furthermore, the controller of the magnetic resonance tomography unit is configured to output an identification for the first system configuration on a machine-readable medium by the output unit.

The identification of the configuration, e.g. on a machine-readable medium, facilitates access to the stored first system configuration and prevents faults due to manual transfer of the data.

The system includes an magnetic resonance tomography unit and a configuration device. The configuration device includes a controller and an input unit.

In an embodiment, the configuration device is configured to identify the first system configuration in the data storage device using the identification. For example, the identification may indicate a link or a path name in the data storage device. However, the identification may contain a key or anonymized identification in order to protect the system configurations. The configuration device is configured to provide a sequence configuration for the magnetic resonance tomography unit that has output the identification as a function of the first system configuration. For example, the configuration unit may load the first system configuration into an internal storage device by the identification and use first system configuration to create a configuration file. However, the configuration device may request individual parameters from the data storage device by the identification.

As the configuration device has access to the correct system information, the compatibility of the generated configuration file with the magnetic resonance tomography unit may be provided.

In an embodiment, the output unit is configured to provide a QR code with the identification, and the input unit is configured to detect the QR code. In a further embodiment, a barcode may be provided instead of the QR code. Optical codes may also be output on a display and be detected by a camera or scanner as the input unit of the configuration device. Other machine-writable and -readable media such as memory chips, magnetic storage devices, optical storage devices or the like may be used. The media may also be secured using cryptological methods against reading out by unauthorized persons or devices.

The machine-readable media, for example, the QR code, allow reliable and safe transmission of the identification. Furthermore, the QR code or a barcode preclude further information from being removed from the magnetic resonance tomography unit unauthorized or, for example, computer viruses from passing into the magnetic resonance tomography unit.

In an embodiment, the method also provides a sequence configuration for the magnetic resonance tomography unit as a function of the first system configuration.

Sequence configuration may refer to a sequence of steps that the magnetic resonance tomography unit has to carry out in order to record an MR image. The sequence configuration may, for example, differ in how quickly a recording should be made and have appropriately fast sequences. Further differences may relate, for example, to the resolution, contrast, the part of the patient to be detected or substances to be detected. It is also conceivable for the sequence configurations to differ, for example, in parameters relating to the patient (e.g., weight or height). The sequence configuration may include, for example, a sequence of instructions that may be executed by the controller of the magnetic resonance tomography unit. Outputs to an operator and steps for processing inputs from an operator may also be included. The sequence configuration may be stored, for example, as a data file, or a plurality of data files that belong together, on the data storage device or also be present in the form of a database. Storage media for storage may be, for example, magnetic, optical or semiconductor storage devices or even memory space in a cloud, abstracted from the respective storage medium.

Magnetic resonance tomography units may differ in hardware options (e.g., in the number of receiving or transmitting channels), and the type and number of receiving or transmitting antennae. Different sequences may be available in the form of software modules for implementation of the magnetic resonance tomography unit. Individual magnetic resonance tomography units may differ in the software version and therefore not understand individual instructions or execute the instructions in a different way with a different result. Different magnetic resonance tomography units may be from different manufacturers.

For providing a sequence configuration for the magnetic resonance tomography unit as a function of the first system configuration, the configuration unit compiles using the information from the first system configuration of the magnetic resonance tomography unit determined via the identification, steps or instructions for execution by the magnetic resonance tomography unit such that the steps or instructions may then also be executed by the magnetic resonance tomography unit determined by the identification. However, the configuration unit may already have ready a sequence configuration, sorted, for example, for certain tasks, in a local storage device, a database or a server. The configuration unit may transform or translate individual steps of an existing sequence configuration, depending on the system configuration, into different instructions and thus adjust to the magnetic resonance tomography unit determined by the identification.

The method may provide that a created sequence configuration may also be executed, without subsequent adjustments or change, on the magnetic resonance tomography unit determined by the identification.

In an embodiment, providing a sequence configuration includes checking by the configuration device whether a step of the sequence configuration is compatible with the first system configuration.

If, for example, the configuration device loads a sequence configuration for a task from a database, the method may define whether the loaded sequence configuration may also be executed by the magnetic resonance tomography unit determined by the identification using the first system configuration.

In an embodiment, the method includes outputting a message to a user of the configuration device as a function of a result of the check, for example, in the case where a planned sequence configuration may not be executed on a magnetic resonance tomography unit determined by the identification.

For example, the configuration device may define when checking that an examination may only be executed with a multi-channel transmitter. If this may be inferred from the first system configuration that the magnetic resonance tomography unit determined by the identification only has a single-channel transmitter, then implementation of the examination and a corresponding sequence configuration is not possible. The method and the configuration device warns the operator as early as during provision in the configuration device, before an error message then occurs on the magnetic resonance tomography unit during a first application of the sequence configuration and valuable examination time is lost.

BRIEF DESCRIPTION OF THE FIGURES

FIG. 2 depicts a flow diagram of an embodiment of a method.

DETAILED DESCRIPTION

Figure 1:
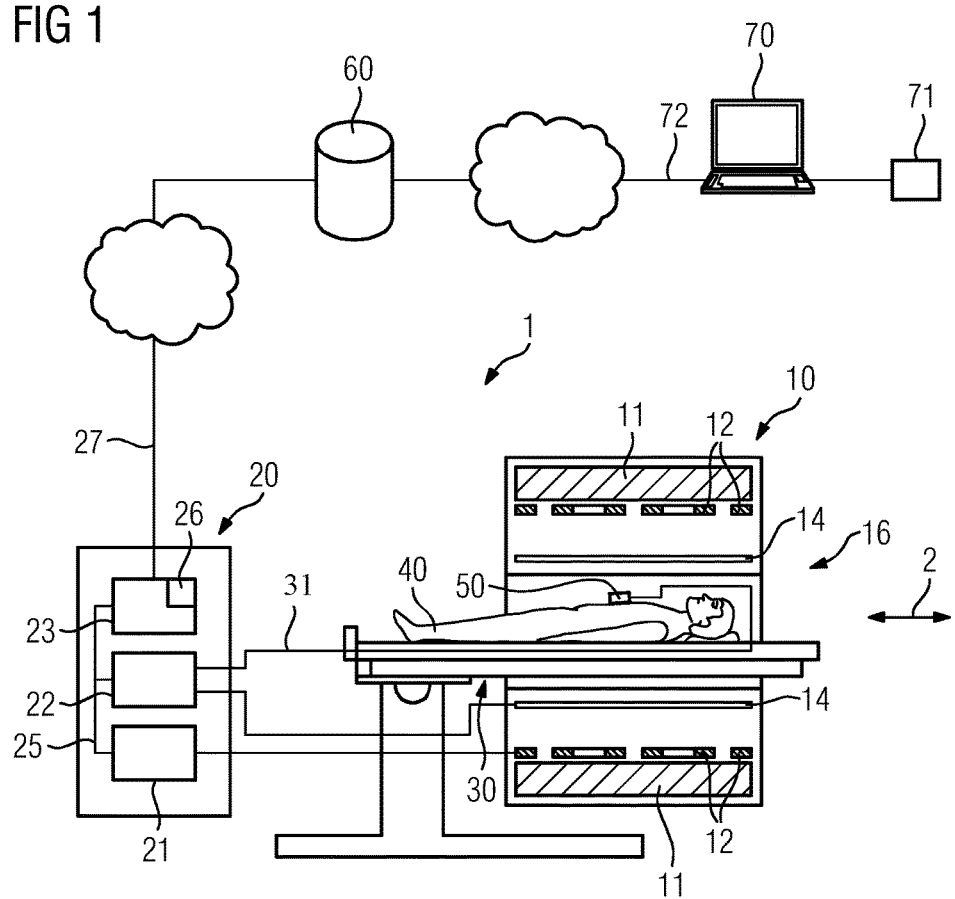
FIG. 1 depicts an embodiment of a system including a magnetic resonance tomography unit and a configuration device.

FIG. 1 depicts a schematic diagram of an embodiment of a magnetic resonance tomography unit 1.

The magnetic unit 10 includes a field magnet 11 that generates a static magnetic field B0 for orientation of nuclear spins of samples or in a body of a patient 40 in a recording region. The recording region is arranged in a patient tunnel 16 that extends through the magnetic unit 10 in a longitudinal direction 2. The field magnet 11 may be a superconducting magnet that may provide magnetic fields with a magnetic flux density of up to 3 T, and possibly above 3 T. Permanent magnets or electromagnets including normal-conducting coils may also be used for lower field strengths.

The magnetic unit 10 also includes gradient coils 12 that for spatial differentiation of the acquired imaging regions in the examination volume are configured to overlay the magnetic field B0 with variable magnetic fields in three spatial directions. The gradient coils 12 are coils including normal-conducting wires that may generate fields in the examination volume that are orthogonal to each other.

The magnetic unit 10 also includes a body coil 14 that is configured to irradiate a high-frequency signal supplied via a signal line into the examination volume and to also receive resonance signals emitted by the patient 40 and emit the signals via signal line. The magnetic resonance tomography unit includes one or more local coil(s) 50 that are arranged in the patient tunnel 16 close to the patient 40.

A control unit 20 supplies the magnetic unit 10 with the various signals for the gradient coils 12 and the body coil 14 and evaluates the received signals.

The control unit 20 includes a gradient controller 21 that is configured to supply the gradient coils 12 with variable currents that provide the desired gradient fields in the examination volume in a temporally coordinated manner via supply lines.

The control unit 20 also includes a high-frequency unit 22 that is configured to generate a high frequency pulse having a predefined time characteristic, amplitude, and spectral power distribution for excitation of a magnetic resonance of the nuclear spins in the patient 40. Pulse powers in the region of kilowatts may be achieved in the process. The individual units are connected to each other by a signal bus 25.

The high-frequency signal generated by the high-frequency unit 22 is fed via a signal link 31 to the examination table 30 and distributed among one or more local coils 50 and emitted in the body of the patient 40 to excite the nuclear spins there.

The local coil 50 receives a magnetic resonance signal from the body of the patient 40 because, due to the small spacing, the signal-to-noise ratio (SNR) of the local coil 50 is better than in the case of receiving through the body coil 14. The MR signal received by the local coil 50 is prepared in the local coil 50 and forwarded to the high-frequency unit 22 of the magnetic resonance tomography unit 1 for evaluation and image acquisition. The signal connection 31 may be used for this purpose, although separate signal connections or wireless transmission may be used. Separate local coils or another antenna may be provided for receiving.

The controller 23 also includes an output unit 26 with which the controller 23 may output a unique first identification of the magnetic resonance tomography unit 1 in a machine-readable form. The output unit 26 may be, for example, a printer, display, or a write unit for a storage medium.

Further, the controller 23 is in data connection with a data storage device 60 via a first data link 27. The first data link 27 may be, for example, a local network, a wireless network, or a data line.

The data storage device 60 is configured to receive a first system configuration from the magnetic resonance tomography unit 1 via the first data link 27, to store the first system configuration, and allocate the first system configuration unambiguously to the magnetic resonance tomography unit 1 by the first identification. Servers, network storage devices, or databases, for example, may be used as the data storage device 60. The data storage device may also be implemented so as to be distributed in a cloud.

A configuration device 70 may also exchange data with the data storage device 60 via a second data link 72, so the configuration device 70 may access the first system configuration. Otherwise, that which was described for the first data link applies to the second data link 72.

The configuration device 70 may be, for example, a computer with a processor, a working memory, and a local data storage device for storing data and programs. The configuration device 70 may also include a drive for data media.

The configuration device 70 may also include an input unit 71 with which the configuration device 70 may detect a first identification. The input unit 71 may have different designs depending on the medium for the first identification. If the first identification is configured, for example, as a barcode or QR code, the input unit 71 may be a camera or scanner. The camera may read the first identification directly from a display of the output unit 26 of the magnetic resonance tomography unit 1 (e.g., if the configuration device 70 is configured as a portable computer). A camera or scanner may, however, likewise detect a first identification on paper. Any data carriers may be used, however, for transmitting the first identification to the configuration device 70. For example, a wireless connection via WLAN, Bluetooth, or Near Field Communication may be used for transmitting the first identification from the magnetic resonance tomography unit 1 to a mobile configuration device 70.

FIG. 2 depicts a schematic flow diagram of an embodiment. The numbering of acts S10 to S80 does not necessarily match the sequence of execution.

At act S10 of the method, the magnetic resonance tomography unit 1 (e.g., the controller 23) stores a first system configuration of the magnetic resonance tomography unit 1 on the data storage device 60. Storage occurs via the first data link 27. The data storage device 60 may be, for example, a server or a cloud, and a transfer protocol, such as FTP or SMB may be used to transmit the system configuration. The first system configuration may be stored, for example, in a local storage device of the controller 23 or be compiled by the controller 23 from individual items of stored information before transmission.

The first system configuration may be provided with a unique identification, so the first system configuration may be distinguished from other system configurations of other magnetic resonance tomography units. The first system configuration may be given a unique file name or for a data field to be provided for an identification.

At act S20, the controller 23 of the magnetic resonance tomography unit 1 generates an identification of the first system configuration. The identification may be used, for example, as a component of the file name or the first system configuration.

At act S30, the controller 23 outputs the identification via the output unit 26 of the magnetic resonance tomography unit 1. The output may be in a form that may be detected by another mechanical device to avoid errors by an operator during transmission. The identification may be encoded in a binary barcode or a QR code, and may be output by a printer as the output unit 26. A code of this kind may also be output via a display and be photographed by an operator, for example, with a smartphone. The identification may be output on a machine-readable storage device such as a USB stick. Conversely, an identification may be output as a string on a display or printer, however, so the operator copies the identification, for example, or at least subsequently inputs the identification manually via a keyboard.

At act S40, the input unit 71 of the configuration device 70 detects the identification. For example, the configuration device 70 may be a mobile computer with a camera as the input unit 70. The camera directly detects the barcode or the QR code, and configuration device 70 determines therefrom the identification using machine recognition algorithms. The input unit 71 may, however, also be a read device for data storage devices. The identification may be read out by the configuration device 70, for example, on a USB stick. The operator may input an identification expressed in text form into the configuration device 70 via a keyboard as the input unit 71.

At act S50, the configuration device 70 accesses the first system configuration in the data storage device 60 via the second data link 72 with the aid of the identification. For example, the identification may be a unique file name. The configuration device 70 may load the first system configuration via a data transfer protocol, such as FTP or SMB, into an internal storage device. The identification may be a key via which the configuration device is given access to individual items of information of the first system configuration in a database as the storage device 60.

At act S60, the configuration device provides a sequence configuration for the magnetic resonance tomography unit 1 as a function of the first system configuration. For example, the configuration device 70 may extract the software version of operating software of the magnetic resonance tomography unit 1 from the first system configuration and use only instructions corresponding to the software version in the sequence configuration. The same applies to the hardware options, for example, without an appropriately large local coil array. A whole-body scan may potentially be interrupted more often in order to reposition the local coil 50.

At act S70, the configuration device 70 checks whether a step of the sequence configuration is compatible with the first system configuration. The syntax of the used instructions may be compared with the software version of the operating software. The comparison may be relevant, for example, if the sequence configuration is, for example, not re-generated at act S60, but is to be taken on by a different magnetic resonance tomography unit 1.

At act S80, the configuration device outputs a message to a user as a function of a result of the check in act S70. For example, the configuration device 70 may output a warning that the sequence configuration may not be executed on the magnetic resonance tomography unit 1. The configuration device 70 may also output a possible reason and/or corrective measures in this regard. For example, the message may include the information that the software version is not compatible and a software upgrade is required in the magnetic resonance tomography unit 1, or that additional hardware may be upgraded to be able to execute, for example, a multi-slice sequence.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance tomography unit comprising:
a data storage device configured to store a plurality of system configurations from a plurality of different magnetic resonance tomography units including the magnetic resonance tomography unit;
a controller configured to store, via a first data link, a first system configuration of the magnetic resonance tomography unit in the data storage device, and output an identification for the first system configuration on a machine-readable medium via an output unit of the controller;
a configuration device comprising a controller and an input unit, wherein the controller of the configuration device is configured to detect the identification for the first system configuration of the magnetic resonance tomography unit from the plurality of system configurations for the plurality of different magnetic resonance tomography units;
the first data link positioned between the data storage device and the controller; and
a second data link positioned between the configuration device and the data storage device.

2. A system for comparing system configurations for a magnetic resonance tomography unit of a plurality of different magnetic resonance tomography units, the system comprising:
the magnetic resonance tomography unit comprising:
a controller and an output unit, wherein the controller is configured to store, via a first data link a first system configuration in a data storage device, and wherein the controller is further configured to output an identification for the first system configuration on a machine-readable medium using the output unit;
a configuration device comprising a controller and an input unit;
the data storage device configured to store a plurality of system configurations for the plurality of different magnetic resonance tomography units;
the first data link between the data storage device and the magnetic resonance tomography unit; and
a second data link between the configuration device and the data storage device,
wherein the controller of the configuration device is configured to detect the identification for the first system configuration of the magnetic resonance tomography unit from the plurality of system configurations for the plurality of different magnetic resonance tomography units.

3. The system of claim 2, wherein the configuration device is configured to identify the first system configuration in the data storage device using the identification, and
wherein the configuration device is further configured to provide a sequence configuration for a magnetic resonance tomography unit that has output the identification as a function of the first system configuration.

4. The system of claim 3, wherein the output unit is configured to provide a QR code with the identification, and the input unit is configured to detect the QR code.

5. A method for comparing a system configuration of a magnetic resonance tomography unit of a plurality of different magnetic resonance tomography units, the method comprising:
storing a first system configuration of a magnetic resonance tomography unit on a data storage device by a controller of the magnetic resonance tomography unit;
generating an identification of the first system configuration by the controller of the magnetic resonance tomography unit;
outputting the identification on a machine-readable medium via an output unit of the magnetic resonance tomography unit;
detecting the identification by an input unit of a configuration device; and
accessing the first system configuration of the magnetic resonance tomography unit from a plurality of system configurations for the plurality of different magnetic resonance tomography units stored in the data storage device by the configuration device via a data link with aid of the identification.

6. The method of claim 5, further comprising:
providing a sequence configuration for the magnetic resonance tomography unit as a function of the first system configuration.

7. The method of claim 6, wherein the providing comprises:
checking, by the configuration device, whether a step of the sequence configuration is compatible with the first system configuration.

8. The method of claim 7, further comprising:
outputting a message to a user of the configuration device as a function of a result of the check.

9. The method of claim 5, wherein the identification comprises a QR code.

10. A non-transitory computer-readable storage medium storing instructions executable by at least one controller of a magnetic resonance tomography unit to compare a system configuration of a magnetic resonance tomography unit of a plurality of different magnetic resonance tomography units, the instructions configured to cause the at least one controller to:
store a first system configuration of a magnetic resonance tomography unit on a data storage device;
generate an identification of the first system configuration;
output the identification on a machine-readable medium via an output unit;
detect the identification by an input unit of a configuration device; and
access the first system configuration of the magnetic resonance tomography unit from a plurality of system configurations for the plurality of different magnetic resonance tomography units stored in the data storage device by the configuration device via a data link with aid of the identification.

11. The non-transitory computer-readable storage medium of claim 10, wherein the instructions are further configured to cause the at least one controller to:
provide a sequence configuration for the magnetic resonance tomography unit as a function of the first system configuration.

12. The non-transitory computer-readable storage medium of claim 11, wherein the instructions are further configured to cause the at least one controller to:
check, by the configuration device, whether a step of the sequence configuration is compatible with the first system configuration.

13. The non-transitory computer-readable storage medium of claim 12, wherein the instructions are further configured to cause the at least one controller to:
output a message to a user of the configuration device as a function of a result of the check.

14. The non-transitory computer-readable storage medium of claim 10, wherein the identification comprises a QR code.

* * * * *